(12) United States Patent
Rome

(10) Patent No.: US 8,083,728 B2
(45) Date of Patent: Dec. 27, 2011

(54) MULTIFUNCTION ADAPTOR FOR AN OPEN-ENDED CATHETER

(75) Inventor: Guy Rome, West Valley City, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 1631 days.

(21) Appl. No.: 10/803,512

(22) Filed: Mar. 18, 2004

(65) Prior Publication Data
US 2005/0209584 A1 Sep. 22, 2005

(51) Int. Cl.
*A61M 25/16* (2006.01)

(52) U.S. Cl. .................. 604/533; 604/523; 604/167.03; 604/167.04; 604/167.06

(58) Field of Classification Search ................. 604/4.01, 604/5.01, 6.1 I, 19–27 I, 30–34 I, 48, 93.01, 604/99.04, 99.07, 164, 167.01, 167.03, 167.04, 604/167.06, 236, 249, 103, 206, 533, 326, 604/905, 523
See application file for complete search history.

(56) References Cited

U.S. PATENT DOCUMENTS

| | | |
|---|---|---|
| 3,176,690 A | 4/1965 | H'Doubler |
| D217,795 S | 6/1970 | Spaven |
| 3,565,078 A | 2/1971 | Vailliancourt et al. |
| 3,572,340 A | 3/1971 | Lloyd et al. |
| 3,650,507 A | 3/1972 | Nyberg et al. |
| 3,672,372 A | 6/1972 | Heimlich |
| 3,805,794 A | 4/1974 | Schlesinger |
| 3,921,631 A | 11/1975 | Thompson |
| 4,000,739 A | 1/1977 | Stevens |
| 4,029,095 A | 6/1977 | Pena et al. |
| 4,068,659 A | 1/1978 | Moorehead |
| 4,112,949 A | 9/1978 | Rosenthal et al. |
| 4,123,091 A | 10/1978 | Cosentino et al. |
| 4,134,402 A | 1/1979 | Mahurkar |
| 4,198,973 A | 4/1980 | Millet |
| 4,233,974 A | 11/1980 | Desecki et al. |
| 4,235,232 A | 11/1980 | Spaven et al. |
| 4,256,106 A * | 3/1981 | Shoor ........................... 604/411 |
| 4,256,116 A | 3/1981 | Meretsky et al. |
| 4,267,835 A * | 5/1981 | Barger et al. .................. 604/250 |
| 4,296,747 A | 10/1981 | Ogle |
| 4,306,562 A | 12/1981 | Osborne |
| 4,340,052 A | 7/1982 | Dennehey et al. |
| 4,387,879 A | 6/1983 | Tauschinski |

(Continued)

FOREIGN PATENT DOCUMENTS

EP 0183396 A1 6/1986

(Continued)

OTHER PUBLICATIONS

Goldfarb et al., "Chronic Venous Access Bedside Placement Technique and Complications," Cancer Practice vol. 2, No. 4, pp. 279-283 (Jul./Aug. 1994).

(Continued)

*Primary Examiner* — Nicholas D Lucchesi
*Assistant Examiner* — Quynh-Nhu H Vu
(74) *Attorney, Agent, or Firm* — Rutan & Tucker, LLP

(57) ABSTRACT

A multifunction adaptor for an open-ended catheter that allows placement of the catheter without risk of air embolism or blood loss through the open (proximal) end of the catheter body. The present design allows passage of a standard guidewire for "over the guidewire" placement techniques and a connection for catheter flushing using a standard syringe.

11 Claims, 5 Drawing Sheets

U.S. PATENT DOCUMENTS

| | | | |
|---|---|---|---|
| 4,391,029 A | 7/1983 | Czuba et al. | |
| 4,411,654 A | 10/1983 | Boarini et al. | |
| 4,412,832 A | 11/1983 | Kling et al. | |
| 4,424,833 A | 1/1984 | Spector et al. | |
| D272,651 S | 2/1984 | Mahurkar | |
| 4,430,081 A | 2/1984 | Timmermans | |
| 4,431,426 A | 2/1984 | Groshong et al. | |
| 4,432,759 A | 2/1984 | Gross et al. | |
| 4,436,519 A | 3/1984 | O'Neill | |
| 4,439,179 A | 3/1984 | Lueders et al. | |
| 4,445,893 A | 5/1984 | Bodicky | |
| 4,449,973 A | 5/1984 | Luther | |
| 4,468,224 A | 8/1984 | Enzmann et al. | |
| 4,473,067 A | 9/1984 | Schiff | |
| 4,490,003 A | 12/1984 | Robinson | |
| RE31,855 E | 3/1985 | Osborne | |
| 4,502,502 A * | 3/1985 | Krug | 137/512.3 |
| 4,512,766 A * | 4/1985 | Vailancourt | 604/167.03 |
| 4,535,818 A * | 8/1985 | Duncan et al. | 137/846 |
| 4,539,003 A | 9/1985 | Tucker | |
| 4,543,087 A | 9/1985 | Sommercorn et al. | |
| 4,553,959 A | 11/1985 | Hickey et al. | |
| 4,557,261 A | 12/1985 | Riigheimer | |
| 4,568,329 A | 2/1986 | Mahurkar | |
| 4,571,241 A | 2/1986 | Christopher | |
| 4,573,974 A | 3/1986 | Ruschke | |
| 4,581,012 A | 4/1986 | Brown et al. | |
| 4,581,025 A | 4/1986 | Timmermans | |
| 4,583,968 A | 4/1986 | Mahurkar | |
| 4,591,355 A | 5/1986 | Hilse | |
| 4,592,749 A | 6/1986 | Ebling et al. | |
| 4,596,559 A | 6/1986 | Fleischhacker | |
| 4,596,571 A | 6/1986 | Bellotti et al. | |
| 4,610,665 A | 9/1986 | Matsumoto et al. | |
| 4,619,643 A | 10/1986 | Bai | |
| 4,623,327 A | 11/1986 | Mahurkar | |
| 4,626,245 A | 12/1986 | Weinstein | |
| 4,643,711 A | 2/1987 | Bates | |
| 4,650,472 A | 3/1987 | Bates | |
| 4,673,393 A | 6/1987 | Suzuki et al. | |
| 4,675,004 A | 6/1987 | Hadford et al. | |
| 4,675,020 A | 6/1987 | McPhee | |
| 4,681,122 A | 7/1987 | Winters et al. | |
| 4,682,978 A | 7/1987 | Martin | |
| 4,692,141 A | 9/1987 | Mahurkar | |
| 4,701,159 A | 10/1987 | Brown et al. | |
| 4,722,725 A | 2/1988 | Sawyer et al. | |
| 4,723,550 A | 2/1988 | Bales et al. | |
| 4,723,948 A | 2/1988 | Clark et al. | |
| 4,726,374 A | 2/1988 | Bales et al. | |
| 4,738,658 A | 4/1988 | Magro et al. | |
| 4,743,265 A | 5/1988 | Whitehouse et al. | |
| 4,747,833 A | 5/1988 | Kousai et al. | |
| 4,753,765 A | 6/1988 | Pande | |
| 4,770,652 A | 9/1988 | Mahurkar | |
| 4,772,266 A | 9/1988 | Groshong | |
| 4,772,268 A | 9/1988 | Bates | |
| 4,776,841 A | 10/1988 | Catalano | |
| 4,784,644 A | 11/1988 | Sawyer et al. | |
| 4,795,426 A | 1/1989 | Jones | |
| 4,798,594 A | 1/1989 | Hillstead | |
| 4,808,155 A | 2/1989 | Mahurkar | |
| 4,842,582 A | 6/1989 | Mahurkar | |
| 4,842,592 A | 6/1989 | Caggiani et al. | |
| 4,850,955 A | 7/1989 | Newkirk | |
| 4,865,593 A | 9/1989 | Ogawa et al. | |
| 4,874,377 A * | 10/1989 | Newgard et al. | 604/167.02 |
| 4,895,561 A | 1/1990 | Mahurkar | |
| 4,909,798 A | 3/1990 | Fleischhacker et al. | |
| RE33,219 E | 5/1990 | Daniell et al. | |
| 4,921,479 A | 5/1990 | Grayzel | |
| 4,929,235 A | 5/1990 | Merry et al. | |
| 4,929,236 A | 5/1990 | Sampson | |
| 4,932,633 A | 6/1990 | Johnson et al. | |
| 4,932,938 A | 6/1990 | Goldberg et al. | |
| 4,935,010 A | 6/1990 | Cox et al. | |
| 4,936,826 A | 6/1990 | Amarasinghe | |
| 4,946,133 A | 8/1990 | Johnson et al. | |
| 4,946,449 A | 8/1990 | Davis, Jr. | |
| 4,952,359 A | 8/1990 | Wells | |
| 4,960,412 A | 10/1990 | Fink | |
| 4,966,588 A | 10/1990 | Rayman et al. | |
| 4,983,168 A | 1/1991 | Moorehead | |
| 4,997,424 A | 3/1991 | Little | |
| 5,007,901 A | 4/1991 | Shields | |
| 5,035,686 A | 7/1991 | Crittenden et al. | |
| 5,041,095 A | 8/1991 | Littrell | |
| 5,053,003 A | 10/1991 | Dadson et al. | |
| 5,053,004 A | 10/1991 | Markel et al. | |
| 5,053,013 A | 10/1991 | Ensminger et al. | |
| 5,053,014 A | 10/1991 | Van Heugten | |
| 5,053,023 A | 10/1991 | Martin | |
| 5,057,073 A | 10/1991 | Martin | |
| 5,059,170 A | 10/1991 | Cameron | |
| 5,064,414 A | 11/1991 | Revane | |
| 5,066,285 A | 11/1991 | Hillstead | |
| 5,071,411 A | 12/1991 | Hillstead | |
| 5,078,688 A | 1/1992 | Lobodzinski et al. | |
| 5,085,645 A | 2/1992 | Purdy et al. | |
| 5,092,857 A | 3/1992 | Fleischhacker | |
| 5,098,392 A | 3/1992 | Fleischhacker et al. | |
| 5,098,393 A | 3/1992 | Amplatz et al. | |
| 5,106,368 A | 4/1992 | Uldall et al. | |
| 5,108,380 A | 4/1992 | Herlitze et al. | |
| 5,112,301 A | 5/1992 | Fenton, Jr. et al. | |
| 5,112,323 A | 5/1992 | Winkler et al. | |
| 5,114,408 A | 5/1992 | Fleischhaker et al. | |
| 5,117,836 A | 6/1992 | Millar | |
| 5,125,904 A | 6/1992 | Lee | |
| 5,135,599 A | 8/1992 | Martin et al. | |
| 5,137,524 A | 8/1992 | Lynn et al. | |
| 5,141,497 A | 8/1992 | Erskine | |
| 5,149,327 A | 9/1992 | Oshiyama | |
| 5,154,701 A | 10/1992 | Cheer et al. | |
| 5,156,592 A | 10/1992 | Martin et al. | |
| 5,156,596 A | 10/1992 | Balbierz et al. | |
| 5,158,545 A | 10/1992 | Trudell et al. | |
| 5,158,553 A | 10/1992 | Berry et al. | |
| 5,160,323 A | 11/1992 | Andrew | |
| 5,163,903 A | 11/1992 | Crittenden et al. | |
| 5,167,634 A | 12/1992 | Corrigan, Jr. et al. | |
| 5,167,637 A | 12/1992 | Okada et al. | |
| 5,169,393 A | 12/1992 | Moorehead et al. | |
| 5,171,222 A | 12/1992 | Euteneuer et al. | |
| 5,180,372 A | 1/1993 | Vegoe et al. | |
| 5,186,431 A | 2/1993 | Tamari | |
| 5,188,593 A | 2/1993 | Martin | |
| 5,190,520 A | 3/1993 | Fenton, Jr. et al. | |
| 5,190,528 A | 3/1993 | Fonger et al. | |
| 5,190,529 A | 3/1993 | McCrory et al. | |
| 5,191,898 A | 3/1993 | Millar | |
| 5,195,962 A | 3/1993 | Martin et al. | |
| 5,197,951 A | 3/1993 | Mahurkar | |
| 5,197,976 A | 3/1993 | Herweck et al. | |
| 5,201,722 A | 4/1993 | Moorehead et al. | |
| 5,205,834 A | 4/1993 | Moorehead et al. | |
| 5,207,650 A | 5/1993 | Martin | |
| 5,209,723 A | 5/1993 | Twardowski et al. | |
| 5,211,633 A | 5/1993 | Stouder, Jr. | |
| 5,215,538 A | 6/1993 | Larkin | |
| 5,221,255 A | 6/1993 | Mahurkar et al. | |
| 5,221,256 A | 6/1993 | Mahurkar | |
| 5,221,263 A | 6/1993 | Sinko et al. | |
| 5,234,410 A | 8/1993 | Graham et al. | |
| 5,242,413 A | 9/1993 | Heiliger | |
| 5,242,430 A | 9/1993 | Arenas et al. | |
| 5,250,033 A | 10/1993 | Evans et al. | |
| 5,251,873 A | 10/1993 | Atkinson et al. | |
| 5,255,691 A | 10/1993 | Otten | |
| 5,273,540 A | 12/1993 | Luther et al. | |
| 5,273,546 A | 12/1993 | McLaughlin et al. | |
| 5,275,583 A | 1/1994 | Crainich | |
| 5,279,597 A | 1/1994 | Dassa et al. | |
| 5,290,294 A | 3/1994 | Cox et al. | |
| 5,304,142 A | 4/1994 | Liebl et al. | |
| 5,304,156 A | 4/1994 | Sylvanowicz et al. | |
| 5,312,337 A | 5/1994 | Flaherty et al. | |

| Patent | Date | Inventor(s) |
|---|---|---|
| 5,312,355 A | 5/1994 | Lee |
| 5,312,357 A | 5/1994 | Buijs et al. |
| 5,320,602 A | 6/1994 | Karpiel |
| 5,324,271 A | 6/1994 | Abluso et al. |
| 5,324,274 A | 6/1994 | Martin |
| 5,330,437 A | 7/1994 | Durman |
| 5,334,157 A | 8/1994 | Klein et al. |
| 5,334,187 A | 8/1994 | Fischell et al. |
| 5,336,192 A | 8/1994 | Palestrant |
| 5,338,313 A | 8/1994 | Mollenauer et al. |
| 5,342,386 A | 8/1994 | Trotta |
| 5,348,537 A | 9/1994 | Wiesner et al. |
| 5,350,358 A | 9/1994 | Martin |
| 5,350,362 A | 9/1994 | Stouder, Jr. |
| 5,350,363 A | 9/1994 | Goode et al. |
| 5,360,397 A | 11/1994 | Pinchuk |
| 5,360,403 A | 11/1994 | Mische |
| 5,364,393 A | 11/1994 | Auth et al. |
| 5,368,574 A | 11/1994 | Antonacci et al. |
| 5,374,245 A | 12/1994 | Mahurkar |
| 5,378,230 A | 1/1995 | Mahurkar |
| 5,380,276 A | 1/1995 | Miller et al. |
| 5,382,241 A | 1/1995 | Choudhury et al. |
| 5,389,090 A | 2/1995 | Fischell et al. |
| 5,391,152 A | 2/1995 | Patterson |
| 5,395,352 A | 3/1995 | Penny |
| 5,397,311 A | 3/1995 | Walker et al. |
| 5,399,172 A | 3/1995 | Martin et al. |
| 5,401,245 A | 3/1995 | Haining |
| 5,405,320 A | 4/1995 | Twardowski et al. |
| 5,405,323 A | 4/1995 | Rogers et al. |
| 5,405,341 A | 4/1995 | Martin |
| 5,407,434 A | 4/1995 | Gross |
| 5,409,463 A | 4/1995 | Thomas et al. |
| 5,409,464 A | 4/1995 | Villalobos |
| 5,409,469 A | 4/1995 | Schaerf |
| 5,409,644 A | 4/1995 | Martin et al. |
| 5,413,561 A | 5/1995 | Fischell et al. |
| 5,415,320 A | 5/1995 | North et al. |
| 5,417,668 A | 5/1995 | Setzer et al. |
| 5,419,340 A | 5/1995 | Stevens |
| 5,423,762 A | 6/1995 | Hillstead |
| 5,429,616 A | 7/1995 | Schaffer |
| 5,437,645 A | 8/1995 | Urban et al. |
| 5,441,504 A | 8/1995 | Pohndorf et al. |
| 5,445,613 A | 8/1995 | Orth |
| 5,453,095 A | 9/1995 | Davila et al. |
| 5,454,409 A | 10/1995 | McAffer et al. |
| 5,460,616 A | 10/1995 | Weinstein et al. |
| 5,472,417 A | 12/1995 | Martin et al. |
| 5,472,418 A | 12/1995 | Palestrant |
| 5,472,432 A | 12/1995 | Martin et al. |
| 5,472,435 A | 12/1995 | Sutton |
| 5,474,099 A | 12/1995 | Boehmer et al. |
| 5,474,540 A | 12/1995 | Miller et al. |
| 5,480,380 A | 1/1996 | Martin |
| 5,484,401 A | 1/1996 | Rodriguez |
| 5,486,159 A | 1/1996 | Mahurkar |
| 5,488,960 A | 2/1996 | Toner |
| 5,496,299 A | 3/1996 | Felix et al. |
| 5,496,346 A | 3/1996 | Horzewski et al. |
| 5,501,676 A | 3/1996 | Niedospial et al. |
| 5,507,733 A | 4/1996 | Larkin et al. |
| 5,509,897 A | 4/1996 | Twardowski et al. |
| 5,514,117 A | 5/1996 | Lynn |
| 5,520,655 A | 5/1996 | Davila et al. |
| 5,520,665 A | 5/1996 | Fleetwood et al. |
| 5,522,806 A | 6/1996 | Schonbachler et al. |
| 5,536,255 A | 7/1996 | Moss |
| 5,538,505 A | 7/1996 | Weinstein et al. |
| 5,542,931 A | 8/1996 | Gravener et al. |
| 5,556,387 A | 9/1996 | Mollenauer et al. |
| 5,569,182 A | 10/1996 | Twardowski et al. |
| 5,599,305 A | 2/1997 | Hermann et al. |
| 5,613,953 A | 3/1997 | Pohndorf |
| 5,613,956 A | 3/1997 | Patterson et al. |
| 5,624,413 A | 4/1997 | Markel et al. |
| 5,632,729 A | 5/1997 | Cai et al. |
| 5,636,875 A | 6/1997 | Wasser et al. |
| 5,637,102 A | 6/1997 | Tolkoff et al. |
| 5,647,857 A | 7/1997 | Anderson et al. |
| 5,651,776 A * | 7/1997 | Appling et al. ............... 604/534 |
| 5,653,698 A | 8/1997 | Niedospial et al. |
| 5,672,158 A | 9/1997 | Okada et al. |
| 5,685,856 A | 11/1997 | Lehrer |
| 5,685,867 A | 11/1997 | Twardowski et al. |
| 5,702,370 A | 12/1997 | Sylvanowicz et al. |
| 5,702,374 A * | 12/1997 | Johnson ...................... 604/533 |
| 5,704,915 A | 1/1998 | Melsky et al. |
| 5,713,867 A | 2/1998 | Morris |
| 5,718,678 A | 2/1998 | Fleming, III |
| 5,718,692 A | 2/1998 | Schon et al. |
| 5,725,506 A | 3/1998 | Freeman et al. |
| 5,735,819 A | 4/1998 | Elliott |
| 5,741,233 A | 4/1998 | Riddle et al. |
| 5,752,937 A | 5/1998 | Otten et al. |
| 5,755,693 A | 5/1998 | Walker et al. |
| 5,755,702 A | 5/1998 | Hillstead et al. |
| 5,766,203 A | 6/1998 | Imran et al. |
| 5,772,628 A | 6/1998 | Bacich et al. |
| 5,772,643 A | 6/1998 | Howell et al. |
| 5,772,678 A | 6/1998 | Thomason et al. |
| 5,776,111 A | 7/1998 | Tesio |
| 5,782,505 A * | 7/1998 | Brooks et al. ............. 285/148.19 |
| 5,782,807 A | 7/1998 | Falvai et al. |
| 5,782,817 A | 7/1998 | Franzel et al. |
| 5,785,694 A | 7/1998 | Cohen et al. |
| 5,797,869 A | 8/1998 | Martin et al. |
| 5,800,414 A | 9/1998 | Cazal |
| 5,807,311 A | 9/1998 | Palestrant |
| 5,810,789 A | 9/1998 | Powers et al. |
| 5,843,031 A | 12/1998 | Hermann et al. |
| 5,843,046 A | 12/1998 | Motisi et al. |
| 5,853,393 A | 12/1998 | Bogert |
| 5,858,007 A | 1/1999 | Fagan et al. |
| 5,865,721 A | 2/1999 | Andrews et al. |
| 5,879,333 A | 3/1999 | Smith |
| 5,885,217 A | 3/1999 | Gisselberg et al. |
| 5,895,376 A | 4/1999 | Schwartz et al. |
| 5,897,533 A | 4/1999 | Glickman |
| 5,911,710 A | 6/1999 | Barry et al. |
| 5,916,194 A | 6/1999 | Jacobsen et al. |
| 5,919,160 A | 7/1999 | Sanfilippo, II |
| 5,921,968 A | 7/1999 | Lampropoulos et al. |
| 5,935,112 A * | 8/1999 | Stevens et al. ............... 604/256 |
| 5,944,695 A | 8/1999 | Johnson et al. |
| 5,944,732 A | 8/1999 | Raulerson et al. |
| 5,947,953 A | 9/1999 | Ash et al. |
| 5,951,518 A | 9/1999 | Licata et al. |
| 5,957,912 A | 9/1999 | Heitzmann |
| 5,961,485 A | 10/1999 | Martin |
| 5,961,486 A | 10/1999 | Twardowski et al. |
| 5,967,490 A | 10/1999 | Pike |
| 5,971,958 A | 10/1999 | Zhang |
| 5,976,103 A | 11/1999 | Martin |
| 5,989,213 A | 11/1999 | Maginot |
| 5,997,486 A | 12/1999 | Burek et al. |
| 6,024,729 A | 2/2000 | Dehdashtian et al. |
| 6,027,480 A | 2/2000 | Davis et al. |
| 6,033,375 A | 3/2000 | Brumbach |
| 6,033,388 A | 3/2000 | Nordstrom et al. |
| 6,036,171 A * | 3/2000 | Weinheimer et al. ...... 251/149.1 |
| 6,053,904 A | 4/2000 | Scribner et al. |
| 6,068,011 A | 5/2000 | Paradis |
| 6,074,374 A | 6/2000 | Fulton |
| 6,074,377 A | 6/2000 | Sanfilippo, II |
| 6,074,379 A | 6/2000 | Prichard |
| 6,083,207 A | 7/2000 | Heck |
| 6,086,555 A | 7/2000 | Eliasen et al. |
| 6,086,570 A | 7/2000 | Aboul-Hosn et al. |
| 6,088,889 A | 7/2000 | Luther et al. |
| 6,090,083 A | 7/2000 | Sell et al. |
| 6,093,154 A | 7/2000 | Burek et al. |
| 6,096,011 A | 8/2000 | Trombley, III et al. |
| 6,099,519 A | 8/2000 | Olsen et al. |
| 6,106,503 A | 8/2000 | Pfeiderer et al. |
| 6,106,540 A | 8/2000 | White et al. |
| 6,120,476 A | 9/2000 | Fung et al. |

| Patent Number | Date | Inventor |
|---|---|---|
| 6,120,480 A | 9/2000 | Zhang et al. |
| 6,132,407 A | 10/2000 | Genese et al. |
| 6,142,981 A | 11/2000 | Heck et al. |
| 6,155,610 A | 12/2000 | Godeau et al. |
| 6,156,016 A | 12/2000 | Maginot |
| 6,159,198 A | 12/2000 | Gardeski et al. |
| 6,162,196 A | 12/2000 | Hart et al. |
| 6,171,281 B1 | 1/2001 | Zhang |
| 6,179,806 B1 | 1/2001 | Sansoucy |
| 6,190,349 B1 | 2/2001 | Ash et al. |
| 6,190,352 B1 | 2/2001 | Haarala et al. |
| 6,190,371 B1 | 2/2001 | Maginot et al. |
| 6,206,849 B1 | 3/2001 | Martin et al. |
| 6,210,366 B1 | 4/2001 | Sanfilippo, II |
| 6,213,988 B1 | 4/2001 | McIvor et al. |
| 6,221,057 B1 | 4/2001 | Schwartz et al. |
| 6,228,060 B1 | 5/2001 | Howell |
| 6,228,062 B1 | 5/2001 | Howell et al. |
| 6,258,058 B1 | 7/2001 | Sanfilippo, II |
| 6,273,871 B1 | 8/2001 | Davis et al. |
| 6,276,661 B1 | 8/2001 | Laird |
| 6,293,927 B1 | 9/2001 | McGuckin, Jr. |
| 6,322,541 B2 | 11/2001 | West et al. |
| 6,331,176 B1 | 12/2001 | Becker et al. |
| 6,332,874 B1 | 12/2001 | Eliasen et al. |
| 6,338,725 B1 | 1/2002 | Hermann et al. |
| 6,344,033 B1 * | 2/2002 | Jepson et al. .................. 604/256 |
| 6,352,520 B1 | 3/2002 | Miyazaki |
| 6,402,723 B1 * | 6/2002 | Lampropoulos et al. ..... 604/256 |
| 6,413,250 B1 | 7/2002 | Smith |
| 6,423,050 B1 | 7/2002 | Twardowski |
| 6,423,053 B1 | 7/2002 | Lee |
| 6,454,744 B1 | 9/2002 | Spohn et al. |
| 6,458,103 B1 | 10/2002 | Albert et al. |
| 6,494,860 B2 | 12/2002 | Rocamora et al. |
| 6,497,681 B1 | 12/2002 | Brenner |
| 6,508,790 B1 | 1/2003 | Lawrence |
| 6,508,807 B1 | 1/2003 | Peters |
| 6,520,939 B2 | 2/2003 | Lafontaine |
| 6,544,247 B1 | 4/2003 | Gardeski et al. |
| 6,551,283 B1 | 4/2003 | Guo et al. |
| 6,562,023 B1 | 5/2003 | Marrs et al. |
| 6,575,960 B2 | 6/2003 | Becker et al. |
| 6,589,262 B1 | 7/2003 | Honebrink et al. |
| 6,592,544 B1 | 7/2003 | Mooney et al. |
| 6,592,558 B2 | 7/2003 | Quah et al. |
| 6,592,565 B2 | 7/2003 | Twardowski |
| 6,623,460 B1 | 9/2003 | Heck |
| 6,626,418 B2 | 9/2003 | Kiehne |
| 6,629,350 B2 | 10/2003 | Motsenbocker |
| 6,632,200 B2 | 10/2003 | Guo et al. |
| 6,638,242 B2 | 10/2003 | Wilson et al. |
| 6,641,574 B2 | 11/2003 | Badia Segura et al. |
| 6,645,178 B1 | 11/2003 | Junker et al. |
| 6,663,595 B2 | 12/2003 | Spohn et al. |
| 6,669,681 B2 | 12/2003 | Jepson et al. |
| 6,682,498 B2 | 1/2004 | Ross |
| 6,682,519 B1 | 1/2004 | Schon |
| 6,689,109 B2 | 2/2004 | Lynn |
| 6,692,464 B2 | 2/2004 | Graf |
| 6,695,832 B2 | 2/2004 | Schon et al. |
| 6,712,796 B2 | 3/2004 | Fentis et al. |
| 6,719,749 B1 | 4/2004 | Schweikert et al. |
| 6,722,705 B2 | 4/2004 | Korkor |
| 6,827,710 B1 | 12/2004 | Mooney et al. |
| 6,843,513 B2 * | 1/2005 | Guala .......................... 285/332 |
| 6,872,198 B1 | 3/2005 | Wilson et al. |
| 6,881,211 B2 | 4/2005 | Schweikert et al. |
| D505,202 S | 5/2005 | Chesnin |
| 6,887,220 B2 | 5/2005 | Hogendijk |
| 6,893,056 B2 * | 5/2005 | Guala ........................ 285/332.1 |
| 6,916,051 B2 | 7/2005 | Fisher |
| 6,916,313 B2 | 7/2005 | Cunningham |
| 6,921,396 B1 * | 7/2005 | Wilson et al. ................. 604/508 |
| 6,932,795 B2 * | 8/2005 | Lopez et al. .................. 604/249 |
| 6,969,381 B2 | 11/2005 | Voorhees |
| 6,971,390 B1 * | 12/2005 | Vasek et al. .................. 604/533 |
| 7,044,441 B2 | 5/2006 | Doyle |
| 7,048,724 B2 | 5/2006 | Grossman et al. |
| 7,094,218 B2 | 8/2006 | Rome et al. |
| 7,163,531 B2 | 1/2007 | Seese et al. |
| 7,182,746 B2 | 2/2007 | Haarala et al. |
| 7,258,685 B2 | 8/2007 | Kerr |
| 7,300,430 B2 | 11/2007 | Wilson et al. |
| 7,347,853 B2 | 3/2008 | DiFiore et al. |
| 7,377,915 B2 | 5/2008 | Rasmussen et al. |
| 7,470,261 B2 | 12/2008 | Lynn |
| 7,578,803 B2 * | 8/2009 | Rome et al. ............... 604/167.04 |
| 7,594,910 B2 | 9/2009 | Butts et al. |
| 7,594,911 B2 | 9/2009 | Powers et al. |
| 2001/0041857 A1 | 11/2001 | Sansoucy |
| 2001/0041873 A1 | 11/2001 | Dopper et al. |
| 2002/0010437 A1 | 1/2002 | Lopez et al. |
| 2002/0077605 A1 | 6/2002 | Fentis et al. |
| 2002/0099326 A1 | 7/2002 | Wilson et al. |
| 2002/0099327 A1 | 7/2002 | Wilson et al. |
| 2002/0128604 A1 | 9/2002 | Nakajima |
| 2002/0147431 A1 | 10/2002 | Lopez et al. |
| 2003/0065288 A1 | 4/2003 | Brimhall et al. |
| 2003/0066218 A1 | 4/2003 | Schweikert |
| 2003/0088213 A1 | 5/2003 | Schweikert et al. |
| 2003/0153898 A1 | 8/2003 | Schon et al. |
| 2003/0187411 A1 | 10/2003 | Constantz |
| 2003/0199853 A1 | 10/2003 | Olsen et al. |
| 2003/0201639 A1 | 10/2003 | Korkor |
| 2003/0225379 A1 | 12/2003 | Schaffer et al. |
| 2004/0065333 A1 | 4/2004 | Wilson et al. |
| 2004/0082923 A1 | 4/2004 | Field |
| 2004/0092863 A1 | 5/2004 | Raulerson et al. |
| 2004/0097903 A1 | 5/2004 | Raulerson |
| 2004/0122418 A1 | 6/2004 | Voorhees |
| 2004/0158208 A1 | 8/2004 | Hiejima |
| 2004/0167463 A1 | 8/2004 | Zawacki et al. |
| 2004/0167478 A1 | 8/2004 | Mooney et al. |
| 2004/0171997 A1 | 9/2004 | Wilson et al. |
| 2004/0172003 A1 | 9/2004 | Wilson et al. |
| 2004/0176739 A1 | 9/2004 | Stephens et al. |
| 2004/0183305 A1 | 9/2004 | Fisher |
| 2004/0186444 A1 | 9/2004 | Daly et al. |
| 2004/0186445 A1 | 9/2004 | Raulerson et al. |
| 2004/0193119 A1 * | 9/2004 | Canaud et al. ................. 604/247 |
| 2004/0243095 A1 | 12/2004 | Nimkar et al. |
| 2005/0049555 A1 | 3/2005 | Moorehead et al. |
| 2005/0080398 A1 | 4/2005 | Markel et al. |
| 2005/0085765 A1 | 4/2005 | Voorhees |
| 2005/0085794 A1 | 4/2005 | Denoth et al. |
| 2005/0095891 A1 | 5/2005 | Schorn |
| 2005/0096585 A1 | 5/2005 | Schon et al. |
| 2005/0113805 A1 | 5/2005 | Devellian et al. |
| 2005/0187535 A1 | 8/2005 | Wilson et al. |
| 2005/0209572 A1 | 9/2005 | Rome et al. |
| 2005/0209581 A1 | 9/2005 | Butts et al. |
| 2005/0209584 A1 | 9/2005 | Rome |
| 2005/0256461 A1 | 11/2005 | DiFiore et al. |
| 2005/0261636 A1 | 11/2005 | Rome et al. |
| 2005/0261664 A1 | 11/2005 | Rome et al. |
| 2005/0261665 A1 | 11/2005 | Voorhees |
| 2006/0015074 A1 | 1/2006 | Lynn |
| 2006/0015086 A1 | 1/2006 | Rasmussen et al. |
| 2006/0084929 A1 | 4/2006 | Eliasen |
| 2006/0129134 A1 | 6/2006 | Kerr |
| 2006/0276773 A1 | 12/2006 | Wilson et al. |
| 2007/0016167 A1 | 1/2007 | Smith et al. |
| 2007/0060866 A1 | 3/2007 | Raulerson et al. |
| 2008/0009832 A1 | 1/2008 | Barron et al. |
| 2008/0200901 A1 | 8/2008 | Rasmussen et al. |
| 2009/0013944 A1 | 1/2009 | Re Fiorentin et al. |
| 2009/0137944 A1 | 5/2009 | Haarala et al. |
| 2010/0010445 A1 | 1/2010 | Powers et al. |
| 2010/0016838 A1 | 1/2010 | Butts et al. |

FOREIGN PATENT DOCUMENTS

| | | |
|---|---|---|
| EP | 0439263 A1 | 7/1991 |
| EP | 0616817 A1 | 9/1994 |
| EP | 1 240 916 A1 | 9/2002 |
| EP | 1240916 A1 | 9/2002 |
| WO | 8401902 A1 | 5/1984 |
| WO | 9421315 A1 | 9/1994 |

| | | |
|---|---|---|
| WO | 9634645 A1 | 11/1996 |
| WO | WO 97/22374 | 6/1997 |
| WO | WO 00/23137 | 4/2000 |
| WO | 02058776 A2 | 8/2002 |
| WO | 03030960 A2 | 4/2003 |
| WO | 03030962 A2 | 4/2003 |
| WO | 03033049 A2 | 4/2003 |
| WO | 2006004943 A2 | 1/2006 |
| WO | 2006066023 A2 | 6/2006 |

OTHER PUBLICATIONS

Hull et al., "The Groshong Catheter: Initial Experience and Early Results of Imging-guided Placement," Cardiovascular Radiology 185:803-807 (1992).

Salem et al., "A New Peripherally Implanted Subcutaneous Permanent Central Venous Access Device for Patients Requiring Chemotherapy," Journal of Clinical Oncology, vol. 11, No. 11, p. 2181-2185 (Nov. 1993).

Twardowski et al., "Measuring Central Venous Structures in Humans: Implications for Central-Vein Catheter Dimensions," The Journal of Vascular Access 3:21-37 (2002).

U.S. Appl. No. 10/803,207, filed Mar. 18, 2004 Non-Final Office Action dated Sep. 19, 2005.

U.S. Appl. No. 10/803,207, filed Mar. 18, 2004 Notice of Allowance dated Apr. 21, 2006.

U.S. Appl. No. 10/803,279, filed Mar. 18, 2004, Advisory Action dated Aug. 22, 2007.

U.S. Appl. No. 10/803,279, filed Mar. 18, 2004, Final Office Action dated May 31, 2007.

U.S. Appl. No. 10/803,279, filed Mar. 18, 2004, Final Office Action dated Oct. 1, 2008.

U.S. Appl. No. 10/803,279, filed Mar. 18, 2004, Non-Final Office Action dated Apr. 2, 2009.

U.S. Appl. No. 10/803,279, filed Mar. 18, 2004, Non-Final Office Action dated Dec. 1, 2006.

U.S. Appl. No. 10/803,279, filed Mar. 18, 2004, Non-Final Office Action dated Jun. 5, 2006.

U.S. Appl. No. 10/803,279, filed Mar. 18, 2004, Non-Final Office Action dated Sep. 20, 2007.

U.S. Appl. No. 10/803,279, filed Mar. 18, 2004, Notice of Allowance dated May 28, 2009.

U.S. Appl. No. 10/803,513, filed Mar. 18, 2004 Non-Final Office Action Jul. 25, 2008.

U.S. Appl. No. 10/803,513, filed Mar. 18, 2004 Notice of Allowance dated Jun. 12, 2009.

U.S. Appl. No. 11/076,564, filed Mar. 8, 2005 Advisory Action Nov. 16, 2006.

U.S. Appl. No. 11/076,564, filed Mar. 8, 2005 Final Office Action dated Aug. 25, 2006.

U.S. Appl. No. 11/076,564, filed Mar. 8, 2005 Final Office Action dated Jul. 27, 2007.

U.S. Appl. No. 11/076,564, filed Mar. 8, 2005 Non-Final Office Action dated Jan. 23, 2008.

U.S. Appl. No. 11/076,564, filed Mar. 8, 2005 Non-Final Office Action dated Dec. 17, 2008.

U.S. Appl. No. 11/076,564, filed Mar. 8, 2005 Notice of Allowance dated Jun. 17, 2009.

U.S. Appl. No. 11/096,553, filed Apr. 1, 2005 Advisory Action dated Aug. 1, 2007.

U.S. Appl. No. 11/096,553, filed Apr. 1, 2005 Final Office Action dated Feb. 27, 2007.

U.S. Appl. No. 11/096,553, filed Apr. 1, 2005 Non-Final Office Action dated Jan. 24, 2006.

U.S. Appl. No. 11/096,553, filed Apr. 1, 2005 Non-Final Office Action dated May 19, 2006.

U.S. Appl. No. 11/096,553, filed Apr. 1, 2005 Non-Final Office Action dated Oct. 10, 2007.

U.S. Appl. No. 11/096,553, filed Apr. 1, 2005 Notice of Allowance dated Mar. 25, 2008.

U.S. Appl. No. 11/122,303, filed May 2, 2005 Non-Final Office Action dated Jun. 8, 2009.

U.S. Appl. No. 11/122,303, filed May 3, 2005 Advisory Action dated Jul. 14, 2008.

U.S. Appl. No. 11/122,303, filed May 3, 2005 Final Office Action dated Apr. 30, 2008.

U.S. Appl. No. 11/122,303, filed May 3, 2005 Non-Final Office Action dated Jan. 20, 2010.

U.S. Appl. No. 11/122,303, filed May 3, 2005 Non-Final Office Action dated Sep. 13, 2007.

U.S. Appl. No. 11/122,303, filed May 3, 2005 Notice of Allowance dated Jul. 9, 2010.

U.S. Appl. No. 11/471,193, filed Jun. 20, 2006, Non-Final Office Action dated Jan. 14, 2010.

U.S. Appl. No. 11/471,193, filed Jun. 20, 2006, Notice of Allowance dated Jul. 26, 2010.

U.S. Appl. No. 12/106,704, filed Apr. 21, 2008 Final Office Action dated Apr. 15, 2010.

U.S. Appl. No. 12/106,704, filed Apr. 21, 2008 Non-Final Office Action dated Apr. 27, 2009.

U.S. Appl. No. 12/106,704, filed Apr. 21, 2008 Non-Final Office Action dated Oct. 22, 2009.

U.S. Appl. No. 12/563,776, filed Sep. 21, 2009 Non-Final Office Action dated Jun. 16, 2010.

Vesely, "Central Venous Catheter Tip Position: A Continuing Controversy," JVIR vol. 14, No. 5, pp. 527-534 (May 2003).

USPTO Office Action for U.S. Appl. No. 11/076,564 mailed Mar. 9, 2006.

USPTO Office Action for U.S. Appl. No. 11/076,564 mailed Aug. 25, 2006.

USPTO Office Action for U.S. Appl. No. 11/076,564 mailed Feb. 9, 2007.

USPTO Office Action for U.S. Appl. No. 11/076,564 mailed Jul. 27, 2007.

Camp, "Care of the Groshong Catheter", Oncol Nurs Forum, vol. 15, No. 6, 1988.

Delmore et al., "Experience with the Groshong Long-Term Central Venous Catheter", Gynecologic Oncology 34, 216-218 (1989).

Malviya et al., "Vascular Access in Gynecological Cancer Using the Groshong Right Atrial Catheter", Gynecological Oncology 33, 313-316 (1989).

*Health Devices* May-Jun. 1996; 25(5-6):214-5.

\* cited by examiner

MULTIFUNCTION ADAPTOR FOR AN OPEN-ENDED CATHETER

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A COMPACT DISK APPENDIX

Not applicable.

FIELD OF INVENTION

The present invention is generally in the field of medical devices. More particularly, the present invention relates to a multifunction adaptor for an open-ended catheter.

BACKGROUND OF THE INVENTION

There are a variety of conditions that require injection of fluids into, or withdrawing fluids from, parts of a body below the surface of the skin of the body. During the procedure, symptomatic gas embolism can occur when undissolved gas (e.g., air, $CO_2$) accumulates in the heart and/or pulmonary arteries. This gas can compromise the circulation of blood through the lungs, causing serious injury or death.

Health Devices May-June 1996; 25(5-6):214-5 reported a case of suspected gas embolism. During a hysteroscopy (performed with a patient under intravenous sedation), the patient gasped for air almost immediately upon uterine insufflation. Based on the clinical signs, the medical staff suspected that the patient's condition was caused by a $CO_2$ embolism that originated in the uterus. However, a follow up investigation revealed that the embolized gas was probably air, not $CO_2$. The air may have been introduced into the patient from the dead space in the tubing set used to connect the insufflator to the hysteroscope. This tubing set was not purged before insufflation began. Health Devices recommended that before delivering a fluid to a patient, one must purge air from tubing sets and instruments. Thus, there is a need for a multifunction adaptor for use with an open-ended catheter wherein the multifunction adaptor can be connected to a syringe to infuse the catheter with saline or purge air from the catheter.

A subcutaneously tunneled catheter is often selected when a catheter might be required to be implanted within a patient for weeks to months. A subcutaneously tunneled catheter can be implanted or removed in the outpatient setting and has a decreased incidence of infection. The typical procedure for implanting the tunneled catheter is by forward tunneling. However, a more preferred method of implanting the tunneled catheter is by reverse tunneling as follows: (a) place the distal end of the catheter within the blood vessel through an entry site; (b) mark an exit locations of a tunnel to be formed in a subcutaneous plane; (c) create the subcutaneous tunnel from the exit to entry site using a tunneler by pushing the sharp point of the tunneler through the skin; (d) attach the proximal end of the catheter to the sharp point of the tunneler; (e) pull the tunneler with the secured catheter from the entry to the exit site, through the subcutaneous tunnel, while gently holding the catheter distal to the cuff; and (f) detach the catheter from the tunneler and attach a bifurcation element thereto.

During the described reverse tunneling technique, the proximal end of a typical catheter tube is open, permitting the entry of air. If the proximal end is clamped, the catheter cannot be reverse tunneled as described. Therefore, there is a need for a multifunction adaptor wherein one end could be attached to the tunneler tip and other end could be attached to the proximal end of an open end of the catheter.

It is common to use an implanted catheter to repeatedly access the vascular system of a patient. A flexible guidewire placed in the vascular system can be used to facilitate placement of the catheter, but its use can prevent capping the catheter to prevent fluid loss from or air entering the vascular system during placement. After catheter placement, it is common to attach a valved cap to the catheter connector(s) to prevent fluid loss from or air entering the catheter and vascular system.

U.S. Pat. No. 6,575,960 (Bleed Back Control Assembly and Method) relates to a Y-valved connector. The 'Y-connector' includes a sealing valve that is normally closed except when accessed with a small diameter tube or wire. The sealing valve does not completely prevent air or fluid leakage, but relies on a second user compressible valve to provide a complete seal.

In short, there are several problems with the current valves. The flow path through the valve is restricted due to a restricted cross-sectional area. There is a dead space above or below the valve where blood accumulates, which makes it difficult to clean the valve. The current valves are not designed for use with a guidewire traversing through the same valve. Also, the valves cannot be accessed multiple times; they are typically screwed on to the catheter and discarded after use.

Therefore, there is a need for a multifunction adaptor that solves the above-mentioned problems and thereby reduces the risk of contamination and permits repeated use of the multifunction adaptor.

SUMMARY OF THE INVENTION

The multifunction adaptor of this invention includes a valved tubing, i.e., a tubing that itself has been shaped to create a valve. The multifunction adaptor is for use with an open-ended catheter such that the multifunction adaptor provides multiple functions, such as, for example: (a) sealing the catheter tube except when being accessed by a syringe or a guidewire to prevent blood loss or air embolism, (b) attaching to a standard luer fitting such as that of syringe to allow flushing of the catheter with a fluid such as saline, (c) operating as a tunneler connector, and (d) providing for an "over the guidewire" placement or replacement technique. In addition, it should be appreciated that other advantageous functions would be provided by the multifunction adaptor of the present invention.

In one embodiment of the present invention, a slit valve hub connector comprises a hub connector and a slit valve, wherein the hub connector is capable of being attached to a catheter tube and the slit valve seals the catheter tube except when being accessed by an introducer to prevent blood loss or air embolism.

In another embodiment of the present invention, a catheter valve hub connector comprises a hub connector and a catheter tube having a slit valve built-in as an integral part of the catheter tube, wherein the slit valve seals the catheter tube except when being accessed by an introducer to prevent blood loss or air embolism.

In yet another embodiment of the present invention, a valve tubing hub connector comprises a hub connector and a tubing having a slit valve built-in the tubing, wherein the hub connector is capable of being attached to a catheter tube and the slit valve seals the catheter tube except when being accessed by an introducer to prevent blood loss or air embolism.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

In the accompanying drawings, reference characters refer to the same parts throughout the different views. The drawings are intended for illustrating some of the principles of providing a multifunction adaptor and are not intended to limit the description in any way. The drawings are not necessarily to scale, emphasis instead being placed upon illustrating the depicted principles in a clear manner.

DETAILED DESCRIPTION OF THE INVENTION

The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The multifunction adaptor may be used for facilitating the introduction or removal of fluid to or from a body. The multifunction adaptor may be temporarily attached to a luer fitting connector of a catheter or it may be permanently attached to the catheter in lieu of the luer fitting connection. The multifunction adaptor could be coupled to a catheter, which may be utilized for chronic excess fluid drainage from a body. In other applications, the multifunction adaptor could be coupled to an implantable electromechanically powered and/or magnetically coupled vesicular pump to permit assisted flow of a fluid into or out of a body. This flow may be uni-directional.

A multifunction adaptor is attached to the open (proximal) end of an attachable catheter tube (single or multi-lumen, silicone or polyurethane). The valve of the multifunction adaptor seals the catheter tube except when being accessed by a syringe (for infusion or aspiration) or a guidewire. One of the purposes of the valve is to seal off the open end of the catheter during placement into the vein. This prevents blood loss or air embolism that may occur if the catheter end is open, as in the case for attachable catheters. A second design feature utilizes the multifunction adaptor to be attached to a standard luer fitting (i.e., syringe). With a syringe attached to the multifunction adaptor, the catheter may be infused (flushed with saline) or aspirated to verify blood flow through the catheter. By utilizing the multifunction adaptor, adapters and clamps are unnecessary. A third design feature allows passage of the catheter/multifunction adaptor assembly over a guidewire. The guidewire can be inserted into the catheter tip (distal end) and passed through the guidewire guide in the valve of the multifunction adaptor to guide the guidewire through the valve slit of the valve and through the multifunction adaptor assembly. Passing the guidewire through the valve minimizes risks associated with blood loss and/or air embolisms possible in an open end catheter design. A fourth design feature allows attachment of the multifunction adaptor to a subcutaneous tunneler without any additional attachments or adapters.

Figure 1:
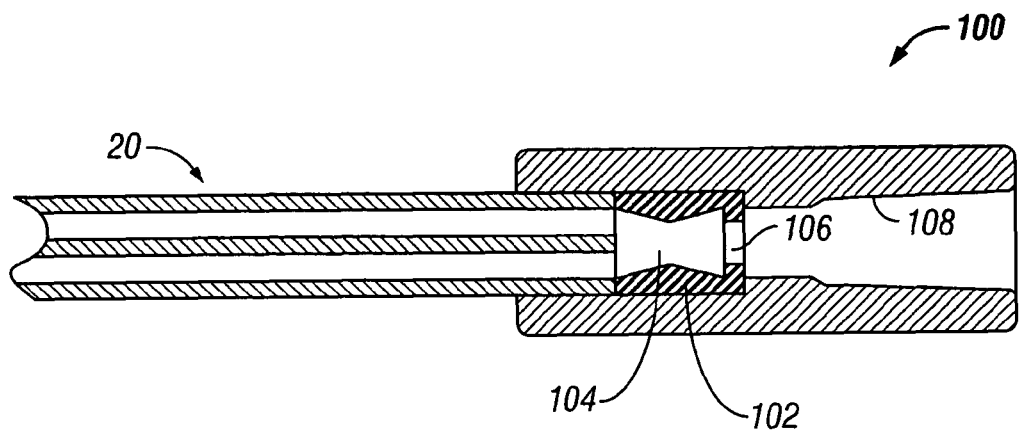
FIG. 1 is a cross-sectional view of a slit valve hub connector according to the present invention attached to a proximal end of a catheter.

The multifunction adaptors of this invention are broadly classified as: (1) a slit valve hub connector; (2) a catheter valve hub connector; and (3) a valved tubing hub connector. FIG. 1 shows a schematic of a slit valve hub connector according to the present invention. Valved hub connector 100 is preferably made of hard material that has rigidity like that of rigid polyurethane and has first and second ends. The valved hub connector 100 is attached at a distal end thereof to an open proximal end of a catheter tube 20, which can be in single or multiple lumen configurations and which are generally made of a polymer material, including silicone and polyurethane. The slit valve hub connector 100 could be attached to the catheter by solvent bonding or by any other method of bonding or overmolding.

The valve 102 is preferably made of silicone and seals the catheter tube except when being accessed by a syringe (for infusion or aspiration) or a guidewire. The valve 102 provides for an "over the guidewire" placement or replacement technique with no blood loss or air embolism. A guidewire can be inserted into the distal end of the catheter and passed through a guidewire guide 104 in the valve hub connector 100 to guide the guidewire through the slit 106 of the valve 102 and through the hub connector 100. In one embodiment, the second end of the slit valve hub connector 100 that is not attached to the open end of the attachable catheter tube may contain a luer taper 108 as shown in FIG. 1. The design of the slit opening could be a single layer slit, a two layer slit or a triple layer design with a slit followed by a hole opening, followed by another slit opening. The hub connector 100 will generally be made of a harder material than will the valve 102. For example, the hub connector 100 may have a hardness in the range of approximately 90 Shore A to 90 Shore D, while the valve 102 may have a hardness in the range of approximately 40 Shore A to 60 Shore A. However, in one embodiment, the hub connector has a hardness in the range of approximately 70 Shore A to 80 Shore A.

Figure 2:
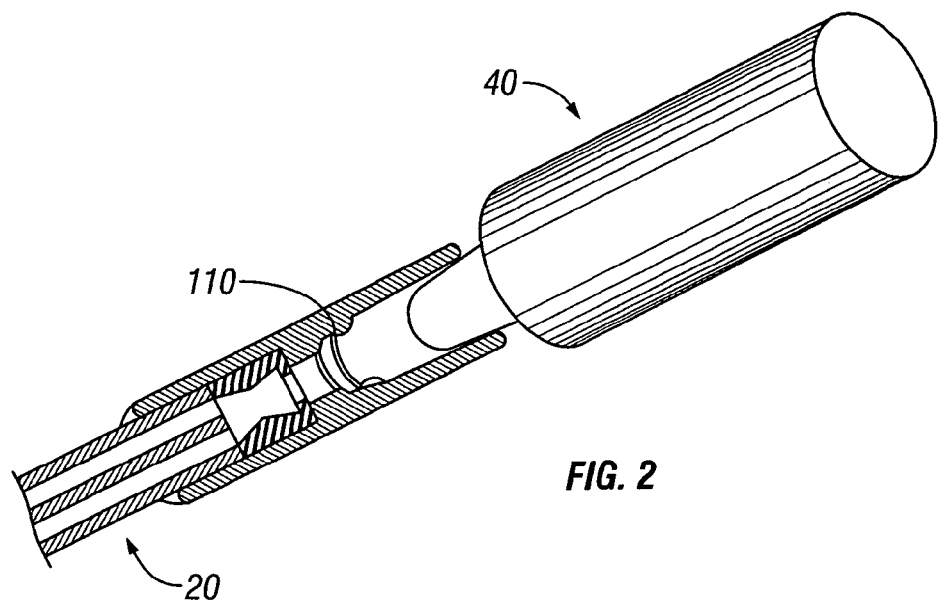
FIG. 2 is a partial cross-sectional view of a syringe connected to the slit valve hub connector of FIG. 1.
Figure 3:
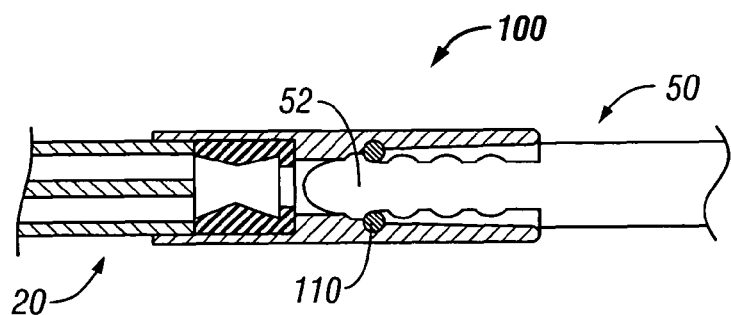
FIG. 3 is a cross-sectional view of a tunneler connected to the slit valve hub connector of FIG. 1.

In valved connector 100, the proximal end thereof not attached or connected to the proximal end of an attachable catheter tube could have luer taper 108 and snap-on piece, such as an O-ring 110, to allow attachment with a standard luer such as a syringe, as shown in FIG. 2, and for attachment of the tip 52 of a tunneler 50 as shown in FIG. 3. While the luer taper and snap-on piece may be preferable for attachment to certain medical instruments, it should be noted that valved connector 100 would be suitable for attachment to, or use with, many different types of medical instruments, including guidewires, syringes and tunnelers, with or without said features.

Figure 4A:
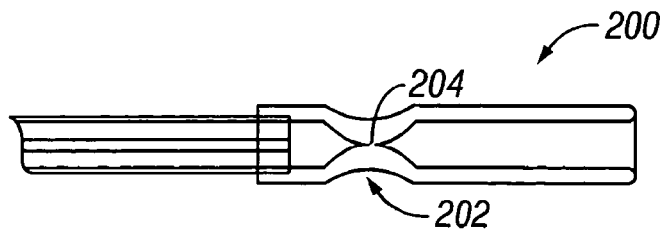
FIG. 4A is a cross-sectional view of another embodiment of a slit valve hub connector according to the present invention.
Figure 4B:
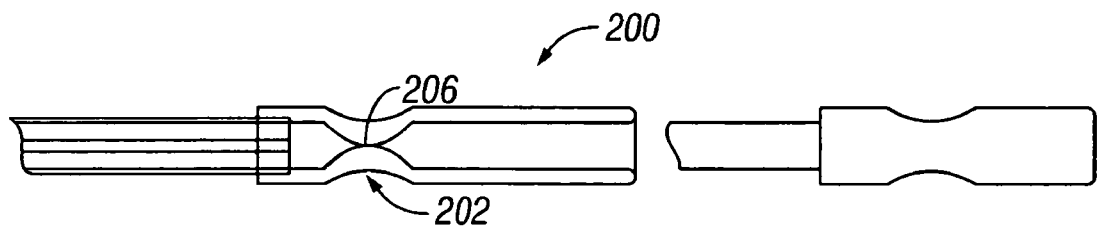
FIG. 4B is a cross-sectional view of yet another embodiment of a slit valve hub connector according to the present invention.

One variation of the multifunction adaptor of the present invention is a slit valve hub connector 200 with a built-in slit valve 206 as shown in FIG. 4B. The valved hub connector 200 is preferably made of soft material that it has rigidity like that of soft polyurethane (e.g., in the range of approximately 60 Shore A to 90 Shore A.) Of course, the hub connector 200 could be made of a harder material, such as in the range of approximately 80 Shore A to 70 Shore D. There are many ways to manufacture the built-in slit valve 206. For example, as shown in FIG. 4A, one method would be to mold the hub connector 200, comprised of a soft material, with a necked portion 202 such that there is initially no opening between the first and second ends as indicated by the solid area 204 therebetween. A slit could then subsequently be formed through the necked portion to form slit valve 206 as shown in FIG. 4B. An alternative method would be to initially create the necked portion 202 with an opening therethrough as shown in FIG. 4B.

Figure 4C:
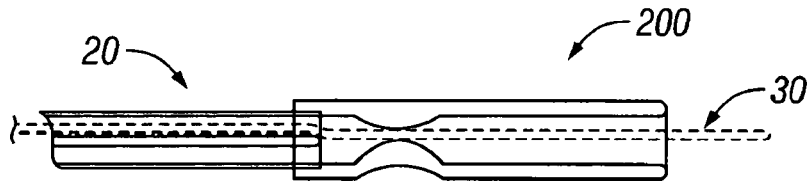
FIG. 4C is a cross-sectional view of the slit valve hub connector with a guidewire passing therethrough.
Figure 4D:
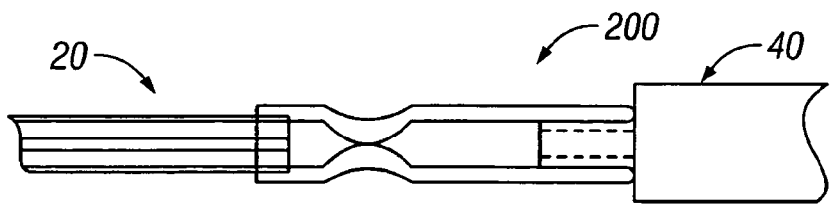
FIG. 4D is a cross-sectional view of a syringe connected to a slit valve hub connector according to the present invention.
Figure 4E:
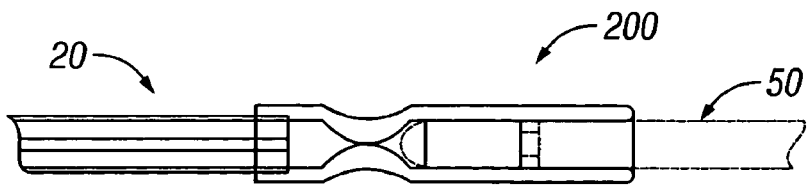
FIG. 4E is a cross-sectional view of a tunneler connected to a slit valve hub connector according to the present invention.

As discussed above, the multifunction adaptor of the present invention can be used to connect to medical instruments to facilitate the use thereof with a catheter. As shown in FIGS. 4C-4E, the valve hub connector 200 can be utilized to allow safe passage of a guidewire 30 through a placed catheter 20 without risk of blood loss or air embolism (FIG. 4C), to connect catheter 20 to a flushing syringe (FIG. 4D) and to connect catheter 20 to a tunneler 50 (FIG. 4E). Of course, the multifunction adaptor of the present invention could be used in conjunction with many other medical instruments as well.

Figure 5A:
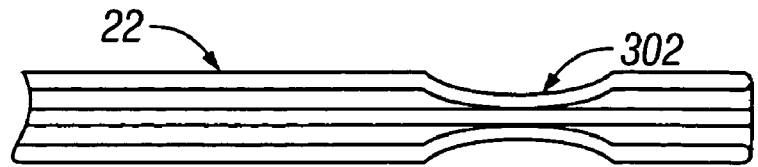
FIG. 5A is a cross-sectional view of a proximal end of a catheter having a valve formed therein.
Figure 5B:
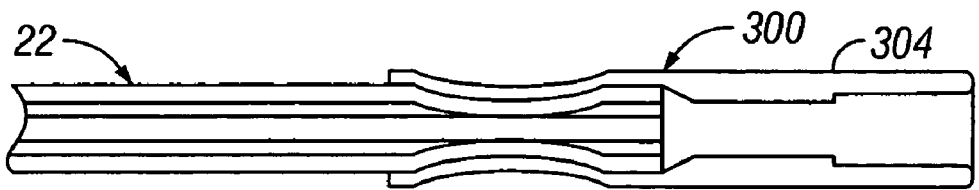
FIG. 5B is a cross-sectional view of the catheter of FIG. 5A with a hub connector overmolded thereon.
Figure 5C:
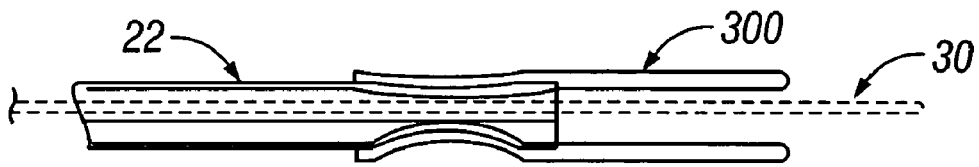
FIG. 5C is a cross-sectional view of the catheter valve hub connector of FIG. 5B with a guidewire passed therethrough.
Figure 5D:
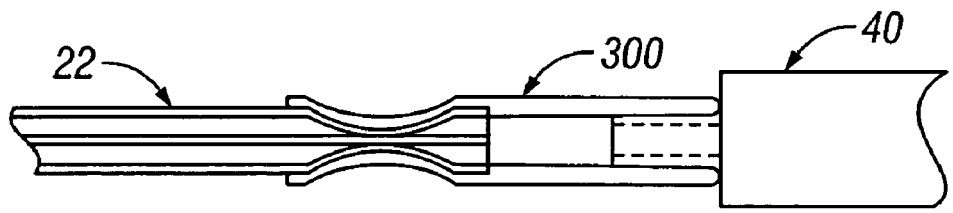
FIG. 5D is a cross-sectional view of a syringe connected to the catheter valve hub connector of FIG. 5B.
Figure 5E:
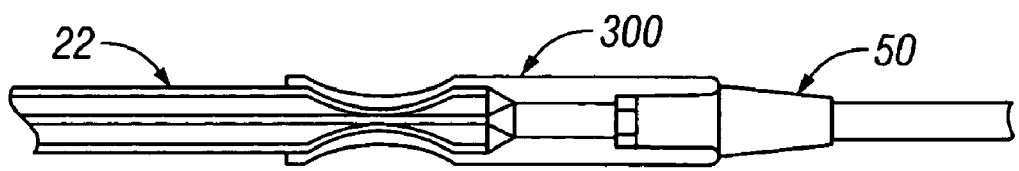
FIG. 5E is a cross-sectional view of a tunneler connected to the catheter valve hub connector of FIG. 5B.

FIGS. 5A-5B illustrate another embodiment of the multifunction adaptor of the present invention, catheter valve hub connector 300. In this embodiment, a thermoplastic catheter tube 22 is thermoformed to create a valve 302 as shown in FIG. 5A. Over-molded over the valve 302 on the proximal end of the tube 22 is a housing 304, resulting in the hub connector 300. It should be noted that although the catheter tube 22 is shown in a dual-lumen configuration, the valve hub connector 300 would equally be applicable to a single or multi-lumen design. The valve 302 seals the catheter tube lumen(s) except when being accessed by a syringe or a guidewire as shown in FIGS. 5C-5D. One of the purposes of the valve 302 is to seal off the open end of the catheter during placement into a blood vessel. The valve 302 prevents blood loss or air embolism that may occur in an open ended catheter. As with the embodiments described above, the catheter hub connector 300 permits attachment of a syringe 40 thereto such that the catheter 22 may be infused (e.g., flushed with saline), as shown in FIG. 5D. By utilizing the valved hub connector, adapters and clamps are unnecessary. As shown in FIG. 5E, the catheter hub connector 300 also permits attachment to a subcutaneous tunneler 50 without any additional attachments or adapters.

Figure 6A:
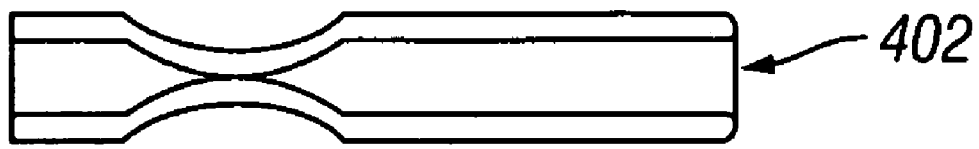
FIG. 6A is a cross-sectional view of a preformed valve tube according to the present invention.
Figure 6B:
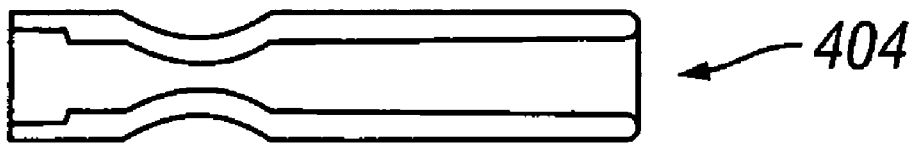
FIG. 6B is a cross-sectional view of a hub connector according to the present invention.
Figure 6C:
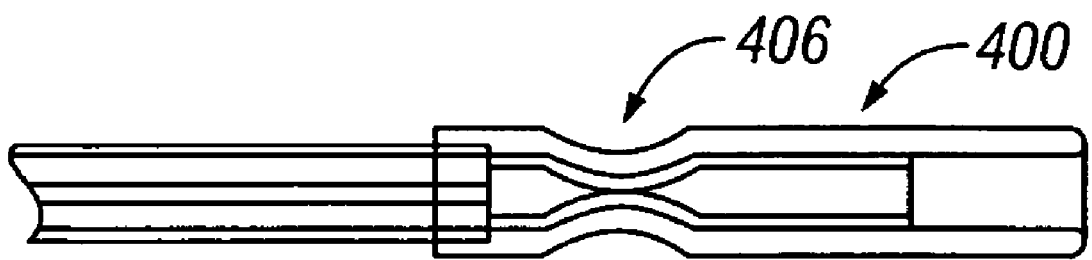
FIG. 6C is a valve tubing hub connector according to the present invention attached to a catheter.

FIG. 6C shows yet another embodiment of the multifunction adaptor of the present invention, valved tubing hub connector 400. The hub connector 400 is manufactured by molding a housing 404 (FIG. 6B) over a preformed valve tube 402 (FIG. 6A). The housing 404 preferably made of hard material (e.g., high durometer silicone), while the valve tube 402 is preferably made of a soft (e.g., thermoplastic) material. Examples of the hardness of materials used for the housing 404 is in the range of approximately 60 to 90 Shore A, while examples for the hardness of the material used for the valve tube 402 is in the range of approximately 40 Shore A to 60 Shore A. The neck portion 406 of the hub connector 400 forms a seal to prevent passage of blood or air therethrough as with the above-described embodiments. The formed hub connector 400 is then attached to catheter 20. Alternatively, the valve tube 402 is first formed and placed into a mold adjacent the catheter 20 for over-molding the housing 404. As with the embodiments described above, hub connector 400 is used in like manner with medical instruments such as guidewires, syringes and tunnelers.

Figure 7A:
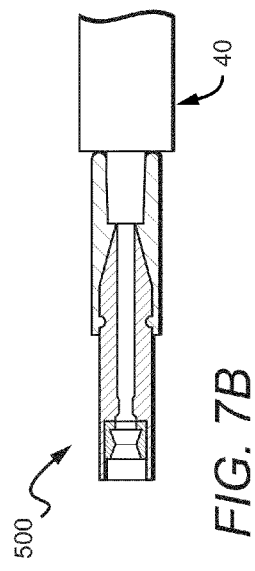
FIG. 7A is a cross-sectional view of another embodiment of the multifunction adaptor according to the present invention.
Figure 7B:
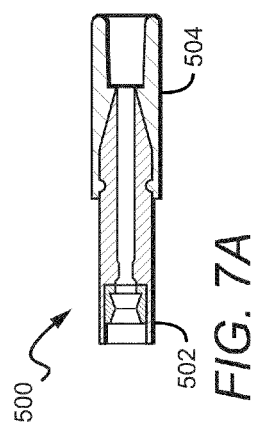
FIG. 7B is a cross-sectional view of a syringe attached to the multifunction adaptor of FIG. 7A.
Figure 7C:
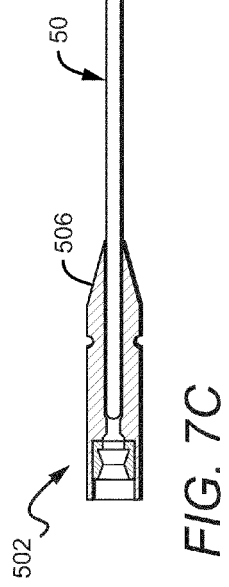
FIG. 7C is a cross-sectional view of a tunneler attached to the multifunction adaptor of FIG. 7A.
Figure 7D:
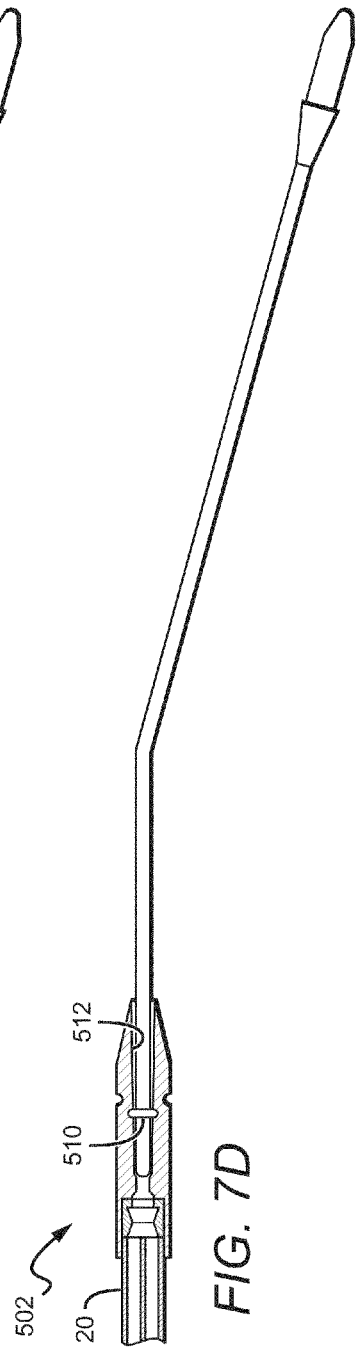
FIG. 7D is a cross-sectional view of a multifunction adaptor attached to a tunneler.

In another embodiment of the multifunction adaptor of the present invention, a tapered connector housing and removable syringe adaptor assembly 500, which allows a reverse tunneled catheter to be flushed and attached to the tip of a tunneler 50, is illustrated in FIG. 7A. It should be appreciated that the tapered connector housing and removable syringe adaptor could be design features for any of the embodiments described herein. The adaptor assembly 500 includes a tapered connector housing 502 and a removable syringe adaptor 504. As shown in FIG. 7B, a syringe 40 is attached to the syringe adaptor 504 for flushing a catheter 20 attached to the distal end of the connector housing 502. After flushing, the syringe adaptor is detached and discarded from the connector housing/catheter assembly. After the catheter is placed and the tunneler is positioned in the subcutaneous tunnel, the proximal end of the connector housing 502 is slid over the tip of the tunneler 50. A compression ring, such as O-ring 510, grips the tunneler tip, allowing the catheter to be withdrawn through the subcutaneous tunnel by pulling the connector 502 through to an exit site. As described above, a wall 512 defining a portion of the passageway proximal of the O-ring may be tapered. The connector housing outside diameter creates the desired subcutaneous tunnel diameter while the tapered tip 506 eases the connector/catheter passage. The design allows use of a standard tunneler, a tunneler with a locking notch, or a tunneler with shallow threads at the tip to allow the tunneler to be removed (unthreaded) from the connector housing.

The multifunction adapter of the present invention may be designed to be small enough to fit within a cylindrical housing with maximum dimensions of 0.5" diameter and 1.0" length. The multifunction adapter may also be designed to be incorporated within a small housing that is compatible with multiple fittings, i.e., luer lock, slip fit, compression, etc. Valve function or performance is not affected by the addition of color or clear housing/components. Component or housing components are not affected by opacity or color. Markings and scales could be used on an as needed basis per application. Device function is not integrally linked to markings, etc. The multifunction adapter of the present invention is sterilizable using standard techniques (EtO, gamma, etc.). The methods of manufacturing the multifunction adapter of the different embodiments include machining or molding the components of the valved tubing and hub connector. While the device is primarily contemplated for use in human patients, the invention will also have veterinary uses or product development purposes in equine, bovine, canine, feline, and other mammalian species.

The present invention has been described above in terms of certain preferred embodiments so that an understanding of the present invention can be conveyed. However, there are many alternative arrangements not specifically described herein, but with which the present invention is applicable. Although specific features have been provided, the present invention would equally be embodied by other configurations not specifically recited herein. The scope of the present invention should therefore not be limited by the embodiments illustrated, but rather it should be understood that the present invention has wide applicability with respect to connector systems generally. All modifications, variations, or equivalent elements and implementations that are within the scope of the appended claims should therefore be considered within the scope of the invention.

What is claimed as new and desired to be protected by Letters Patent of the United States is:

1. A catheter assembly, comprising:
   a catheter including at least one lumen;
   a connector including a distal end attached to a proximal end of the catheter and a passageway in fluid communication with the at least one lumen, a proximal portion of the passageway including an engagement feature configured to connect an end of an instrument to the connector, a distal portion of the passageway including a built-in valve longitudinally fixed with respect to the connector having a closed proximal end with a slit and an open distal end, the valve proximal end distal of the engagement feature; and
   a tunneler, wherein the engagement feature engages a tip of the tunneler upon insertion of the tunneler tip into the proximal portion of the passageway.

2. The catheter assembly according to claim 1, wherein the valve includes a wall defining a lumen from the proximal end to the distal end, the wall configured to guide a proximal end of a guidewire from the valve distal end through the slit in the valve proximal end.

3. The catheter assembly according to claim 1, wherein the connector comprises a material having a hardness in the range of about 90 Shore A to about 90 Shore D, and wherein the valve comprises a material having a hardness in the range of about 40 Shore A to about 60 Shore A.

4. The catheter assembly according to claim 1, wherein the engagement feature comprises an O-ring, and wherein a wall defining the proximal portion of the passageway proximal of the O-ring is tapered.

5. The catheter assembly according to claim 1, wherein the connector includes an tapered outer surface at a proximal end thereof.

6. The catheter assembly according to claim 5, further comprising a syringe adaptor including a distal end configured to slide over the tapered proximal end of the connector housing and a proximal opening to receive a male luer.

7. The catheter assembly according to claim 1, wherein the valve opens by insertion of a medical device through the valve.

8. The catheter assembly according to claim 1, wherein the valve proximal end is longitudinally fixed with respect to the connector.

9. The catheter assembly according to claim 1, wherein the valve proximal end is fixed relative to the engagement feature.

10. The catheter assembly according to claim 1, wherein the engagement feature includes a projection into the passageway.

11. The catheter assembly according to claim 10, wherein the projection has a reduced diameter relative to an inside diameter of the passageway on a proximal side and a distal side of the projection.

* * * * *